United States Patent [19]
Chalifoux

[11] Patent Number: 5,820,376
[45] Date of Patent: Oct. 13, 1998

[54] DENTAL POST HAVING CUTTING EXTENSIONS, AND METHOD OF USE

[76] Inventor: Paul R. Chalifoux, 6 Wellesley Ave., Wellesley, Mass. 02181

[21] Appl. No.: 802,201

[22] Filed: Feb. 18, 1997

Related U.S. Application Data

[63] Continuation-in-part of Ser. No. 679,984, Jul. 16, 1996.

[51] Int. Cl.[6] ................................................ A61C 5/08
[52] U.S. Cl. ........................................ 433/221; 433/225
[58] Field of Search ................................. 433/220, 221, 433/224, 225

[56] References Cited

U.S. PATENT DOCUMENTS

| | | | |
|---|---|---|---|
| 1,589,994 | 6/1926 | Simmons | 433/221 |
| 1,612,227 | 12/1926 | Simmons | 433/221 |
| 2,705,837 | 4/1955 | Gerlach | 433/221 |
| 4,479,783 | 10/1984 | Weissman | 433/221 |
| 4,729,736 | 3/1988 | Weissman | 433/221 |

FOREIGN PATENT DOCUMENTS

| | | | |
|---|---|---|---|
| 292422 | 2/1930 | Italy | 433/221 |
| 391683 | 5/1933 | United Kingdom | 433/221 |

Primary Examiner—Nicholas D. Lucchesi
Attorney, Agent, or Firm—Paul J. Cook

[57] ABSTRACT

A dental post having a top portion and a lower portion. The lower portion has cylindrical sections of differing diameters and extensions. Grooves formed on the section walls from extensions allow engagement of extensions in a canal wall. Cutting surfaces on the post prepare a canal and serve as vents for cement introduced into a canal of a tooth. The post functions both as a bur and as a dental post.

18 Claims, 6 Drawing Sheets

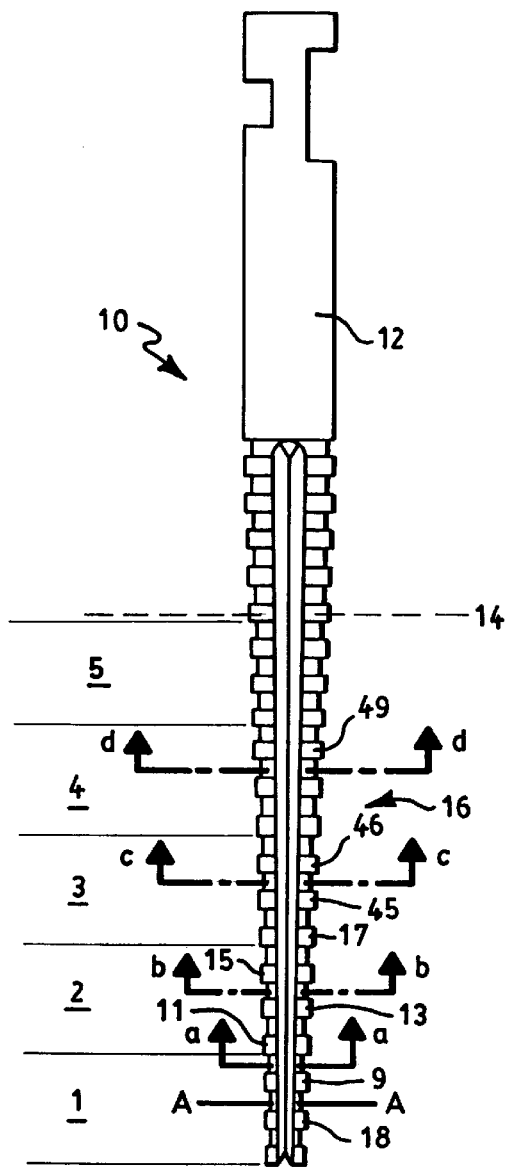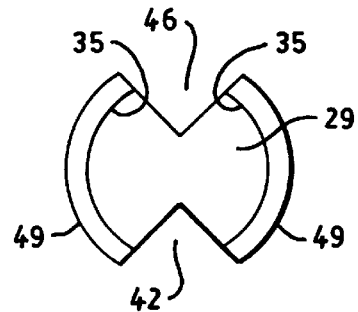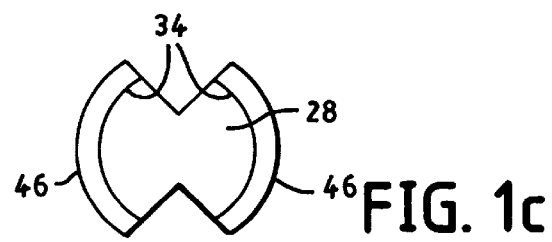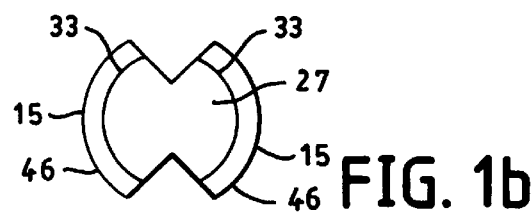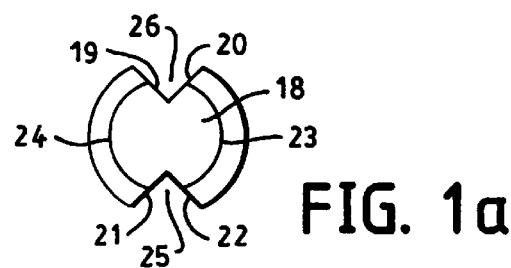
FIG. 1
FIG. 1a
FIG. 1b
FIG. 1c
FIG. 1d

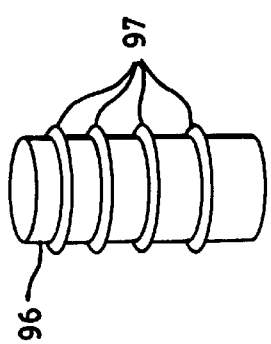
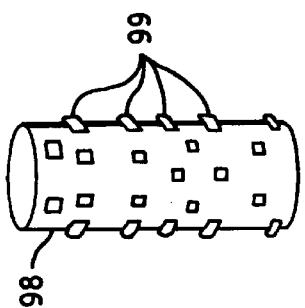
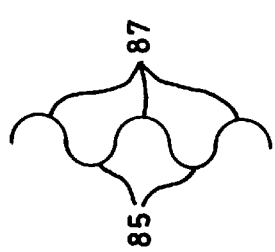
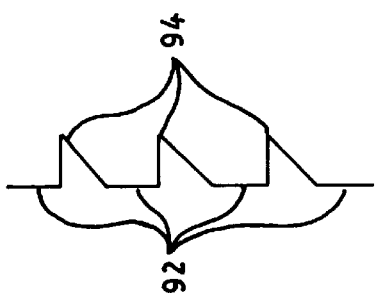
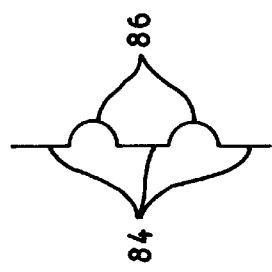
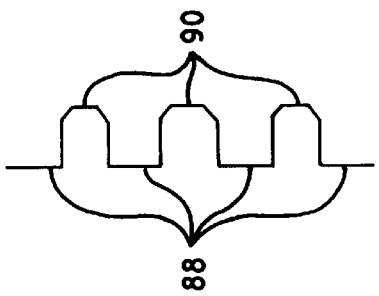
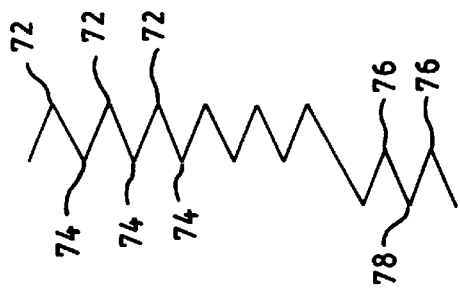
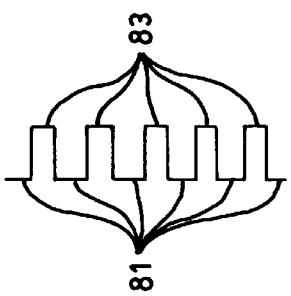
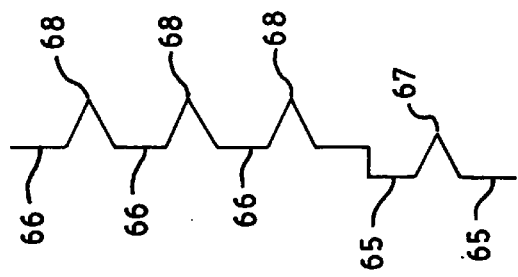
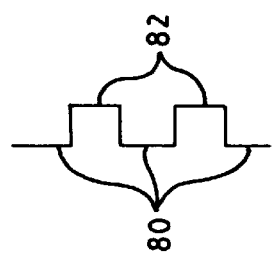

DENTAL POST HAVING CUTTING EXTENSIONS, AND METHOD OF USE

REFERENCE TO RELATED APPLICATION

This application is a continuation-in-part of application Ser. No. 08/679,984, filed Jul. 16, 1996.

BACKGROUND OF THE INVENTION

This invention relates to a dental post construction which can be inserted into a tooth stub and which is utilized to improve retention of a dental restoration built onto the tooth stub. More particularly, this invention relates to a vented dental post having cutting and non-cutting surfaces, including surface extensions.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a bore into which a dental post can be inserted. Presently available dental post include grooves on their surface designed to improve retention of the post within the tooth stub. Present grooves accept cement for aided retention. Dental cement is employed in the bore in conjunction with the dental post to secure the post in the tooth stub. A portion of the post extends above the tooth stub upper surface so that a dental prosthesis formed on the tooth stub can be retained.

Preformed posts are posts which are premade to specific dimensions with matching burrs having cutting surfaces. The burrs have a matching diameter to the post and prepare the root to accept a post. A post is then tried in the root and cut to the appropriate length and removed from the bore. Cement is spun into the canal with a device referred to as a lenticulo spiral, placed directly with a syringe and/or placed directly on the post. The post is placed in the canal and held in position until excess cement extrudes and the cement hardens. Most preformed posts require placing filling material around the top of the post to transfer strength from the post to the crown. This procedure is referred to as the core build up or post and core procedure.

There are many problems which are encountered when utilizing preformed posts. These include:

An inaccurate fit develops with present bur technology.

Potential for perforation of the root is great with present burrs.

There is inadequate resistance to rotational forces on the post.

Root fracture caused by lateral stresses occurs.

There is weak transfer of strength from the post to the crown positioned on the post.

There easy breaking of the cement to root canal wall interface.

An accurately drilled hole results in good proximity of the post to the canal walls with a thin cement layer to provide greater success in properly positioning the post. Generally, it is desirable to have a cement layer within a 5 to 20 micron thickness range to provide desired post retention and maximum cement compressive strength. The hole is inaccurate if tipping or vibrating of the bur occurs during root preparation as occurs with present drilling systems. This is undesirable as it adds to the failure rate of preformed post systems. Drilling a straight hole for a straight post in a curved canal or drilling a hole which does not align with a canal can lead to perforation of a root and loss of a tooth. All posts must resist normal compressive, lateral, retentive and rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth. Some systems try to make posts oval or non-symmetrical at the top but do not supply dependable resistance and retention form. Cement merely provides suction to hold a post in position. The strength of the cement becomes a weak point to the root-post-crown relationship. Constant repeated forces of chewing causes potential breakdown on the cement and cement interfaces with subsequent cement wash out and crown post failure. An uneven or excessive amount force can cause root fracture and tooth loss. In addition, forceful placement of cement type posts without proper venting of cement can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is inducted for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include: An increased chance of root fracture. The cast post is expensive. There is an increased possibility of root perforation. The cast post may not provide good resistance to rotational forces.

All posts need to provide venting of cement as a post is placed into a tooth bore. A cast post is very precise fitting so it is difficult for cement to vent, lateral forces can fracture the root and/or the post will not be fully seated as excess cement remains in the tooth bore. In addition, any bubbles or inaccuracies from the casting process can cause a poor fit and root fracture. Fracture is also caused by a wedging effect of taper design. Cast posts are much more expensive as compared to preformed posts because there are laboratory fees and increased time required to treat the patient. For a cast post, an appointment is needed for an impression in addition to an appointment for post placement. The patient cost of a cast post is double the cost of a preformed post. The doctors laboratory cost may be five to ten times the cost of a preformed post.

Preparation of a root canal space must be free of any undercuts or removal of a cast post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

Present posts are further classified as being parallel or tapered. Parallel posts have the sides of the post parallel to each other. They form the strongest retention of any post design because the suction created is strong. However, because they are parallel and the same diameter throughout while root canal spaces are tapered, it is necessary to destroy more tooth structure than a tapered design. Tapered posts have sides angled relative to each other such that the bottom of the post has the smallest diameter. While there are less retention forces for tapered posts than parallel posts, more tooth structure is maintained which results in a stronger root. Unfortunately, tapered posts produce a wedging force when force is applied on the top of the post which results in increased root fracture.

Other present systems are defined as active or passive. A passive post is placed into a tooth bore and surrounded by cement with no engagement of tooth structure. An active post, which is usually a threaded post, actively engages tooth structure. Threaded posts create wedging effects at the threads which can create cracking. Threaded posts also can unthread if counter clockwise forces are placed onto it.

U.S. Pat. No. 361,315 discloses a dental post having a stepped diameter construction and a cement vent. The post is used in conjunction with a burr having a shape similar to that of a post. The burr is provided only with cutting surfaces contacting the wall of the root canal.

U.S. Pat. 5,066,230 and 4,990,088 discloses a dental tool which functions as both a dental post and a burr for forming a bore in a tooth stub. The tool comprises a shaft having alternating cutting surface areas along its length which are either a 100% cutting surface area contacting a root canal wall (or a 100% non-cutting surface area contacting a root canal wall.)

U.S. Pat. No. 5,145,373 discloses a dental post having a spiral groove along its length. The groove functions as a cement vent, a means for retaining the post in the root canal and as a threading means to aid in post removal in the event removal is necessary.

Accordingly, it would be desirable to provide a dental post which can be inserted into the bore of a tooth stub while maintaining maximum amount of tooth structure. It would be desirable to provide such a post which avoids application of wedging forces. It would be desirable to provide such a post with maximum retentive strength. It would be desirable to provide such a post which is capable of cutting a tooth canal wall while eliminating the need for a separate burr. It would be further desirable to provide a post which provides extensions which engage a root bore for added retention. It would be desirable to provide a post which provides accurate cutting and which permits cement venting.

SUMMARY OF THE INVENTION

This invention provides a dental post having an upper stem section and a lower portion, a portion of which can be removed. The lower portion includes extensions which can be positioned within grooves of a canal of a tooth. The stem portion extends above a top surface of a tooth stub after the post is positioned within the tooth stub. The lower portion is then positioned into a canal which has been lengthened and extensions positioned into grooves formed in the bore wall. Alternatively, a lower section of the lower portion is removed and the lower portion then rotated to form grooves in the bore wall to position the extension therein.

The lower section is formed of multiple sections having different diameters and having extensions. The sections of the lower section can be parallel sided but generally decrease in diameter from the top of the post to the bottom of the post.

The lower portion has parallel side surfaces and is formed of multiple sections having differing diameters and having extensions. The sections have uniform cutting ability or can have a section which provides guidance to direction of cutting. In one alternative, at least one section of the multiple sections has a surface which either is completely non-cutting or has a sufficiently large surface area which is non-cutting so that it functions as a guide for the lower portion to cause it to traverse the tooth bore path rather than directing the post through a wall of the bore. This section which functions as a guide is referred to herein as the non-cutting section. The cutting surfaces are formed by the edges of spaces in the post surface. The spaces function as a vent for cement used to place the post in the tooth bore. When the non-cutting section includes cutting surfaces, cutting is only effected by the non-cutting section when excessive lateral force is applied to the post by the user or when small irregularities on the wall of the tooth bore are encountered. Providing this non-cutting section, prevents passage of the post through the bore wall. The remaining sections of the lower portion provide the primary function of limited cutting of the tooth bore. A bottom section of the lowermost portions is removed prior to inserting it into the tooth bore. Alternatively, the post is left intact and the canal lengthened with an matching gates glidden, peeso reamer or like burr. When the lower portion is inserted into the bore, it is rotated so that the extensions form grooves into the bore walls into which the extensions fit. Rotation can be accomplished with slow drills or by hand rotation. Since the sides of the sections from which extensions extend are parallel, little or no wedging force is exerted on the tooth as compared to a bur or post which is characterized by converging sides with the smallest diameter being at the bottom of the lower section and the largest diameter being at the top of the lower section.

The non-cutting section of the lower portion can be the top section, bottom section or positioned at an intermediate section on the lower portion. It is preferable to position the non-cutting section at the lowest section of the post. The non-cutting surface as used herein refers to the solid outside surface of each section but excluding the cutting edges. Each section of the lower portion is formed from a cylindrical section having at least one portion comprising an open space that extends the length of the cylindrical section. The edges defining a line of demarcation between the space and the solid cylindrical section comprise the cutting surfaces. The primary cutting surfaces are positioned at the bottom of each section where the space, lower surface of the section and the cylindrical wall converge. Each segment removes only a small portion of the bore wall. Thus, the cutting function is distributed over all of the sections of the lower portion. By distributing the cutting forces rather than concentrating the cutting forces trauma to the root is minimized.

After the bore is formed, a lowest section on the lowermost portion is removed to render the post shorter than the original post length. The shortened post is inserted in the bore so that each post portion is at least partially positioned in a bore section formed from an adjacent lower post portion. The edges of the extension which edge comprises the cutting surfaces that form surfaces in the bore wall when the inserted post is oscillated. Upon completion of the rotation or oscillation, the post extension fit into the formed groove. Since the cutting surfaces are formed to subtend spaces on the post surface, the effective post diameter is flattened so that it is out of round. This flattening permits a section of the lower portion to fit into the next smaller diameter of the tooth bore so that the extension can form grooves. Alternatively, the post can cut new subsections in the wall of the tooth bore by rotation or oscillation with controlled finger pressure. Alternatively, pressure can cause compression of tooth bore dentin structure to allow post advancement.

Since the tooth bore produced after the dentin is removed from root canal treatment usually has tapered walls with the smallest diameter being at the bore bottom and the largest diameter being at the bore top, when the multisection post is first inserted into the bore, the non-cutting section will immediately contact the bore wall or will contact the bore wall shortly after cutting is initiated. The effective post taper defined by a tangent line to the lower portion of the post matches or closely approximates the normal or prepared taper of a canal. For example, the cutting surfaces do not engage the canal walls until the post extends about 80% down the canal when the lower portion is divided into five equal heights. Cylinders contact with a lower portion having fewer cylinders occurs prior to this 80% while contact with more cylinders occurs at greater that about 80% extension. This is because the non-cutting section is sized to a diameter normally encountered in a tooth bore at the bore height where the non-cutting section is positioned.

If a canal has portions which are parallel side walls, each section of the lower portion will remove a small amount of tooth structure within a tooth bore prior to the next section engaging the same area and removing more tooth structure as the burr is moved in a downward direction. Removal of small amounts of tooth structure in a progressive pattern minimizes force onto a tooth bore which could cause cracks to occur.

For convenience, this invention will be described specifically hereinafter with regard to the preferred embodiment of this invention wherein the non-cutting section is positioned at the lowest position of the lower portion. This embodiment is preferred since the guiding function of the non-cutting section is effected immediately when the post is inserted into the tooth bore when it is desired to shape the tooth bore by cutting its walls to a shape which conforms to the shape of the post. However, it is to be understood that the non-cutting section can be positioned at any portion along the length of the lower section or not included at all. The length of the non-cutting section generally comprises between about 1 and 50%, preferably between about 10 and 25% of the lower portion length.

In the preferred embodiment, the lowest section of the lower portion has the highest portion comprising non-cutting surface area. The portion of each section comprising the non-cutting surface area decreases from the lowest section to the highest section of the lower portion. The change in the ratio can be continuous or stepwise wherein each of a plurality of portions of the lower section has a constant ratio of non-cutting surface area to cutting surface area. As used herein, the term stepwise means that the ratio is constant for a short length of the lower section and then changes to a different ratio at a second short length of the lower section. That is, the ratio changes in steps each having a short length along the total length of the lower section.

The lowest section of the lower portion effects a small amount of cutting or no cutting while functioning primarily as a guide through the preexisting tooth bore as a result of the contact between the non-cutting and the bore wall. Each succeeding section of the lower portion above the lowest portion provides additional cutting of the bore wall so that the final cut bore has essentially the same shape as the lower portion of the post to be positioned within the bore.

The cutting surfaces are formed from one or more grooves extending into the post. In use, the tooth stub is initially shaped with standard endodontic procedures including endodontic files or reamers, gates gliddens peeso reamers or the like. Endodontic filling material is removed and the canal is shaped with a gates glidden or peeso reamer which results in a canal bore wall with an irregular surface. The dental post of this invention then is inserted into the formed canal and rotated to effect cutting of the canal wall and guidance of the post through the canal rather than through the outer wall of the tooth stub. The resultant bore conforms to the shape of the outer surface of the lower portion of the post so that it is tightly fit into the bore. The post is removed from the bore which is then washed to remove debris. The post lower portion, a portion of which can be removed is reinserted into the tooth bore, placed apically and rotated to have extensions form grooves in the tooth bore. Alternatively, placement of cement and formation of grooves can be accomplished simultaneously, Cement is then introduced into the bore. The post is trimmed to proper length or notched for breaking off in the canal. The post is then placed into the bore and excess cement exudes from the bore through spaces between the cutting surfaces. A top portion of the post is removed such as by cutting or removing a press fit top section so that a crown or the like can be positioned on the exposed portion of the post.

BRIEF DESCRIPTION OF THE DRAWINGS

FIG. 1 is a cross sectional view of the post of this invention.

FIG. 1a is a cross-sectional view of FIG. 1 taken along line a—a.

FIG. 1b is a cross-sectional view of FIG. 1 taken along line b—b.

FIG. 1c is a cross-sectional view of FIG. 1 taken along line c—c.

FIG. 1d is a cross-sectional view of FIG. 1 taken along line d—d.

FIG. 5a, 5b, 5c, 5d, 5e, 5f, 5g, and 5h are cross section views to illustrate alternative extensions of this invention.

FIG. 5i and 5j are side views illustrating different extensions of this invention.

DESCRIPTION OF SPECIFIC EMBODIMENTS

Figure 2:
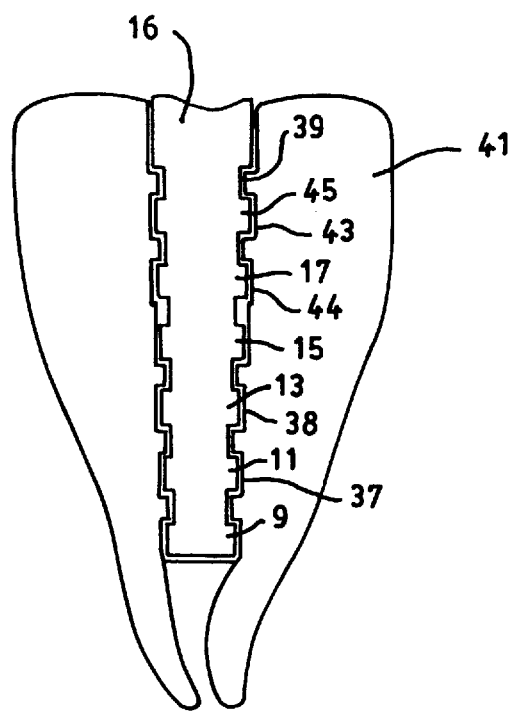
FIG. 2 a side view of the post of FIG. 1 positioned in a tooth.

The dental post of this invention includes an upper stem portion for attachment of a dental prosthesis and a lower portion with extensions. The upper stem portion is designed in any of the usual manners to include flanges, through splits, matching cores, wings, irregular shapes or the like.

The lower section is designed to have at least two subsections. The effective diameter of the subsections decreases in the vertical direction away from top section. That is, the effective diameter of a subsection is less than the effective diameter of all the subsections above it. The subsections can have straight surfaces or curved including parallel surfaces, conical surfaces, circular surfaces of the like. The result of having the effective subsection diameter decrease in the vertical direction away from the top section is that the lower section tapers inwardly to avoid wedging effect on the tooth bore wall. Decreasing the effective diameter of the lower section of the post allows for conservation of more tooth structure, greater root strength and, therefore, less chance of root fracture and tooth loss. The lower section of the post can have any cross sectional shape such as triangular, square, rectangular, oval, or the like.

Cutting extensions can traverse as a solid unit over non-cutting areas or be interrupted into several extensions. The extensions can have many shapes to include cross sections (in any direction) such as triangular, square, rectangular, hexagonal, round, oval, or the like. Cutting extensions which traverse across a non-cutting area effectively forming a horizontal bar provide a means to cut a horizontal slot into dentin. The upper edge of the extension engages the upper edge of the slot for maximum retention. Threads can unscrew if counterclockwise forces are placed on a post. Horizontal extensions do not have this problem. In addition, if the extensions are rounded, they do not create the a wedging effect as occurs with threads when lateral forces are placed on a top section of a post.

The extensions of this invention can be of any size. Preferably the extensions are not of a length to create a diameter larger that the diameter of the section above it. Extensions which are larger in radius from the center of the post than the section above it would create a matching section of a root bore larger than the section above it. When the post has a lower portion removed, the extensions of the upper segment could not engage the bore wall as the bore wall diameter would be larger than the double radius or diameter of the extensions. Preferably, extensions of a section will be of a smaller radius from the center of the post as compared to the radius of the extensions above it.

In another embodiment, the lower section of the post has cutting extensions which cut a path and slot in the dentin and remain embedded in the dentin for retention. The top section can be provided with a preattached core. The post can be covered with enough extensions, such as aluminum oxide or diamond coating, to cut its own path in the root structure.

In another embodiment, the post includes an attached full or partial flange. Holes in the flange can be provided for placement of matching sized pins.

In still another embodiment, the post includes a through slot up or down with extensions which match to indentations formed in the root canal by a special bur.

In still another embodiment, the post includes a through slot up or down with extensions which cut their own indentation into the dentin of root canal space.

In still another embodiment, the lowest portion functions (a) as a guide to position the post within a tooth canal or bore, (b) as a bur to shape the dental canal to conform to the outer surface of the post and (c) as a dental post to support the upper stem portion in a desired position on the tooth. A lowermost section of the lower portion either has no cutting surface or has the highest portion of its surface area being non-cutting surface. This lowermost section functions to guide the post within the tooth canal from which dentin has been removed rather than guiding the post through a wall of the canal. The lower portion of the post has a decreased portion of its circumference functioning as a cutting surface rather than a non-cutting surface in a direction beginning from the lowermost section and extending to the uppermost section of the lower portion.

The open space between the cutting surfaces on the post function as a vent for cement within the canal after cement has been placed therein and the post is subsequently inserted into the canal. Since the lower most section of the post functions to guide the post through the canal and the cutting surfaces cut into the walls of the canal to conform the canal shape to the outer surface shape of the lower portion of the post, the space between the post and the tooth canal can be maintained within a desired range of about 1 micron to about 200 microns, preferable between about 5 microns to about 40 microns so that the desired cement thickness between the wall and post can be attained. The width of this space can be easily controlled by minimizing moving the post gently from side to side during post rotation when cutting canal walls. Fine control can be further enhanced by hand rotation using the top section which fits into the drill as a handle. Cement thickness is an important factor to control successful post function. If cement is too thick, side forces on the top portion of the post transfer compressive force on the cement which leads to cement failure. Thin cement layer prevents or minimizes compressive failure of cement.

A single section or each section of the lower portion has extensions extending from it surfaces. The edges of the extension function as cutting surfaces. After the original bore is formed, a lowermost section of the lowest portion is removed so that the post is shorter than its original length. Alternatively, the canal is lengthened in the apical portion. This permits each section to be inserted into a bore portion lower than the bore portion originally formed by the bore section so that the cutting surfaces of the extensions can engage tooth structure. There are alternative techniques which allow each section to be inserted into a bore portion lower than the bore portion originally formed by the bore section which include (a) an oval bore being formed by the effective oval cross section of the post. This effect is cause because of the areas cut away for cutting surfaces and cement venting, (b) pressing a post apically and compressing or cutting dentin and (c) effecting enough rotation to cut a new bore subsection. If oscillating is performed by finger pressure there is more control than with a drill and a more precise fit is accomplished as tipping is minimized.

Subsequent to cutting, the canal is cleared of debris such as with a water stream, dried, and cement is then inserted therein. Finally, the post is reinserted into the canal with or without rotational force that would cause cutting and excess cement is vented from the canal through the space between the cutting surfaces. The post is then rotated to cut or engage existing horizontal grooves in the bore wall.

As set forth above, the dental post of this invention includes an upper portion and a lower portion. The upper portion is designed in any conventional manner to include flanges, through splits, matching cores, wings, irregular shapes or the like. The lower portion is designed to have at least two sections. The effective diameter of the subsections decreases in the vertical direction away from upper portion. That is, the effective diameter of a given section is less that the effective diameter of all the sections above it. The result of having the effective section diameter decrease in the vertical direction away form the upper portion is that the lower portion tapers inwardly and avoids a wedging effect on the tooth bore wall. Decreasing the effective diameter of the lower portion of the post allows for conservation of more tooth structure, greater root strength and, therefore, less chance of root fracture and tooth loss. The extensions of the post extend into the bore groove. This permits the post section to be retained in the root canal subsection. If extensions engage root bore wall, forces which try to dislodge, referred to as loss of retention, a post there is compressive force of the upper part of an extension onto the upper part of a groove. If there is cement between the extension and a groove, the force onto the cement in the same area would be compressive. Presently, passive posts exert only shear or tensile forces onto cement with dislodging forces.

In a preferred embodiment, the extension is formed by horizontal grooves carved into each subsection. The resulting extensions traverse from a cutting area across non-cutting areas to the next non-cutting area. Cross section shapes can include triangular, square, rounded square, rectangular, hexagonal, round, oval, or the like. Dislodging forces to the post, such as would occur when chewing sticky foods, would be resisted by the top of an extension against the top of a groove in the bore. Compressive forces to the post, such as would occur with chewing down onto teeth, would be further distributed to the bottom of an extension to a bottom of a groove in addition to the lower segments of each subsection. Lateral forces of chewing as results from food deflecting off cusp inclinations, would be resisted by extensions into grooves. Lateral forces create a fulcrum point about which rotation tries to occur. For example, if contact of a post occurred at the bottom of a tooth bore on the bottom to the lingual or tongue side, force to the lingual top section of a post rotates the post about this point to the facial (away from the lingual). In this case, extensions to the lingual side of the post will have their upper side engage the upper part of a groove while the extensions to the facial will have their bottom sections engage the bottom of the matching groove. Rotational forces are resisted by the cutting edges of extensions abutting cement which fills the cutting/ cement venting areas and the matching open groove areas which are not filled with extensions.

This invention also provides for posts having other features conventionally used on posts including extensions, cutting extensions, threads, interrupted threads, through slots, venting slots, indentations, a disk or flange at the top of the post which is positioned on the top of a tooth, used with indentations created in the root canal walls, or the like.

Referring to FIGS. 1, 1a, 1b, 1c, 1d, and FIG. 2 the post 10 includes an upper portion 12 positioned above dotted line 14 and a lower portion 16 positioned below dotted line 14. The lowermost section 18 of lower portion 16 includes subsections 18, 27, 28 and 29 or length 1, 2, 3, 4, and optionally 5. The lowermost section 18 of lower portion 16 include cutting surfaces 19, 20, 21 and 22 and has the highest proportion of the surface area comprising non-cutting surfaces 23 and 24 since spaces 25 and 26 between the cutting surfaces are small. The lowermost section 18 also can have no cutting surfaces and it functions to guide the post 10 through a tooth canal rather than into a wall of the canal. The proportion of the surface of the post sections 27, 28, and 29 comprising non-cutting surface 33, 34, and 35, decrease when moving in a direction toward the uppermost section 29 or lower portion 16. In addition, the diameter of the post sections progressively increase from post section 18 to post section 29.

After cutting the canal, the post 10 is removed from the canal which is then washed to remove debris therefrom. The portion of lower section 1, below line A—A is removed to shorten the lower portion 16. This permits the extension 9, 11 and 13 to fit into the canal portion formed by the lower most portion 1. Extension 9 is the original size of the bore section so it does not engage the bore wall. The post 10 then is rotated or oscillated and grooves 37, and 38 are formed in the wall of canal 39 of tooth 41 by extensions 11 and 13. Additional grooves 43 and 44 also are formed into which the extensions 17 and 45 fit. Extension 15 does not engage the canal wall as it did initial preparation of this subsection. This permits improved retention of the post 10 in tooth 41. Cement is inserted into the canal and the lower section 16 then is inserted into the canal. Excess cement is vented from the canal through spaces 25 and 26, through the spaces intervening sections 27, 28, and 29 and lastly through spaces 42 and 46 in the uppermost section 29. Thus, the post 10 functions as a bur, a post and a vent for excess cement.

In addition, the post provides a means for shaping the tooth canal to precisely conform to the outer shape of the lower section 16 of the post 10 including the extensions. The post eliminates the need for a separate bur which has problems of tolerances in manufacturing and additional cost, insures precise formation of a canal shape which accommodates the post and provides a means for venting excess cement and provides a means for improved retention in the bore. The provision of a bur, post and cement vent means a single dental apparatus not only significantly reduces the needed apparatus for implementing the post but also significantly reduces the time needed for subjecting a patient to a procedure for building a prosthesis on a tooth stub.

Extensions form a general cylinder shape in the matching tooth bore section when rotated rapidly in a drill. They cut individual paths when rotated slowly.

Referring to FIG. 2, the lower portion 16 is shown positioned in tooth 41 with the extensions 11 and 13 positioned in grooves 37 and 38 formed by the cutting edges of extensions 11 and 13.

Figure 3A:
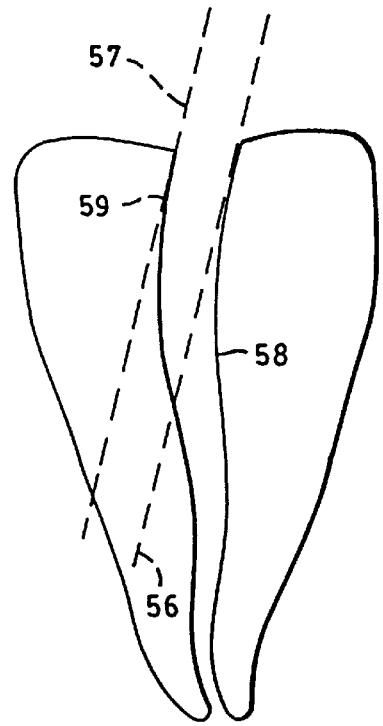
FIG. 3 illustrates a common result obtained with a bur of prior art.
FIG. 3b illustrates the result obtained with the dental post of this invention.
Figure 3B:
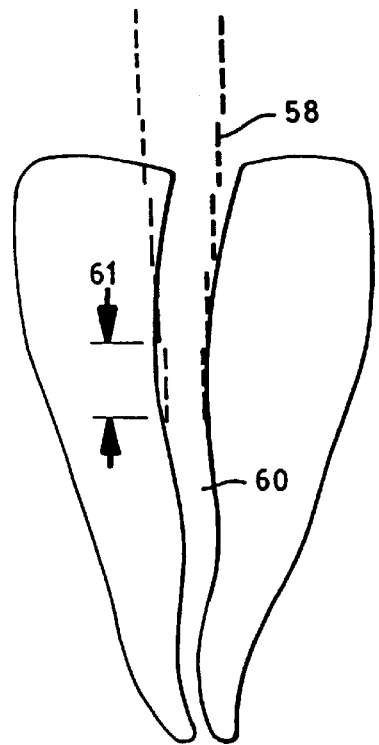

Referring to FIG. 3a and 3b, a common result which occurs without the guiding functions of the post of this invention. When excess cutting surfaces are provided at the lower portion 56 of a post or bur 57, the post or bur 57 will not follow the path of tooth canal 58 to insure incorrect positioning of post 57 but drill through side wall 59. In contrast, as shown in FIG. 3b, the post 63 of this invention will follow the path defined by the canal 60 since the leading section 61 of the post 63 follow the path defined by canal 60 rather than passing through a canal wall as shown in FIG. 3a.

Figure 4A:
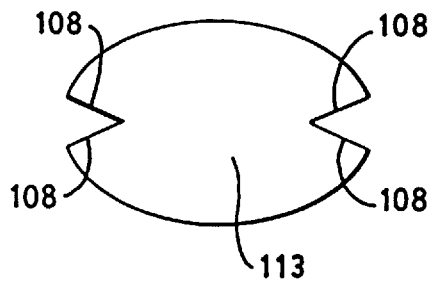
FIG. 4, 4a and 4b illustrate the cutting function of the post of this invention.
Figure 4:
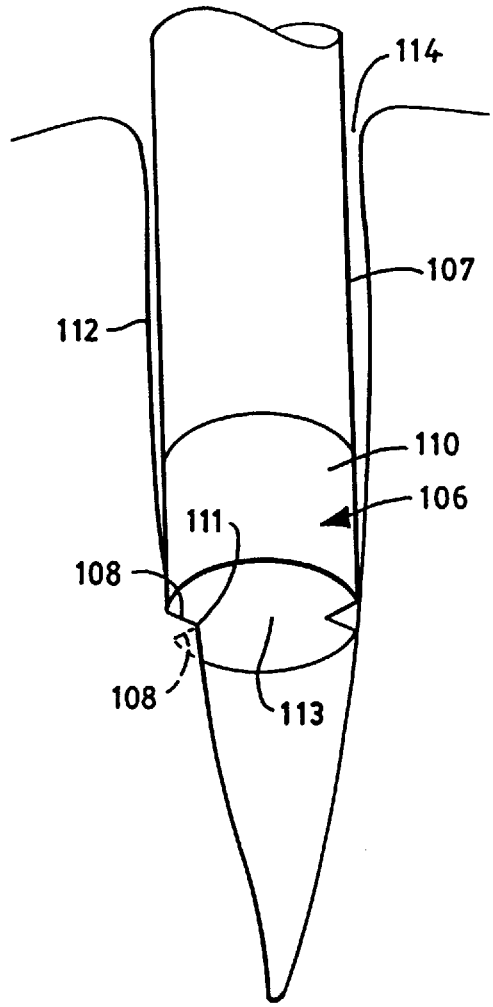
Figure 4B:
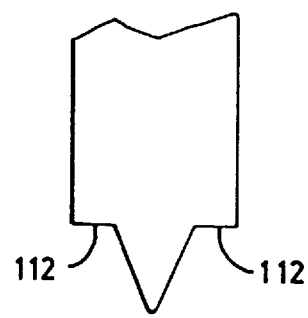

The limited penetration of the post of this invention into a canal wall is illustrated in FIGS. 4, 4a, and 4b. The lowermost section 106 of post 107 includes cutting surfaces 108 having a depth extending from the outer surface 110 of section 106 to apex 111. This cutting surface configuration limits the depth into the canal wall 112 to which section 106 can extend. The bottom non-cutting surface 113 provides a stop means for the post 107 to limit the depth the post 107 extends into canal 114.

Referring to FIGS. 5a, 5b, 5c, 5d, 5e, 5f, 5g, and 5h, different extension shapes are shown. FIG. 5a shows a cross section of triangular extensions 68 with subsection wall 66. The next lower section shows extension 67 and section wall 65. FIG. 5b shows triangular extensions 72 which join together to form apexes 74. The next lower section shows extension 76 and section wall 78. FIG. 5c shows squares extensions 82 extending from section wall 80. FIG. 5d shows rectangular extensions 83 and section wall 81. FIG. 5e shows round extensions 86 and section wall 84. FIG. 5f shows round extensions 87 and rounded section wall 85.

FIG. 5g shows square with rounded corners extensions 90 and section wall 88. FIG. 5h shows alternative extensions 94 with section wall 92. FIG. 5i shows a subsection 96 with extensions 97 which extend the length of the non cutting surface. FIG. 5j show a subsection 98 with a series of interrupted extensions 99.

Figure 6C:
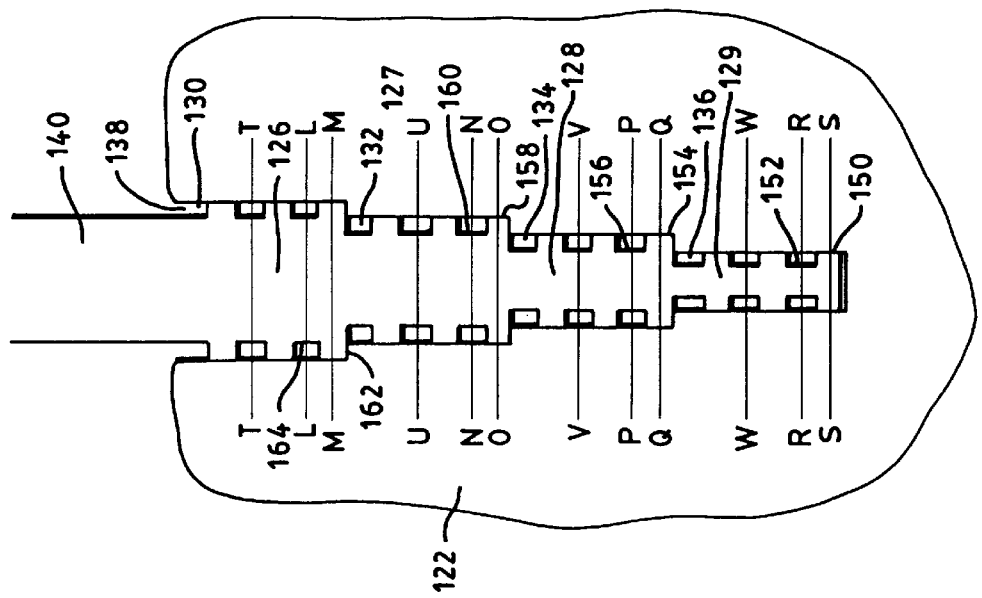
FIG. 6c is a cross section view of the post of FIG. 6a in the root of FIG. 6b after initial preparation.
Figure 6B:
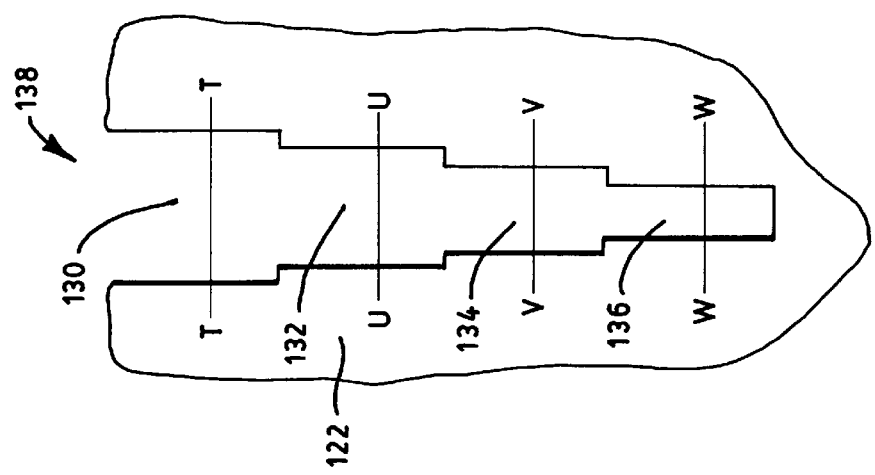
FIG. 6b is a cross section view of a prepared bore in a tooth by a post of this invention.
Figure 6A:
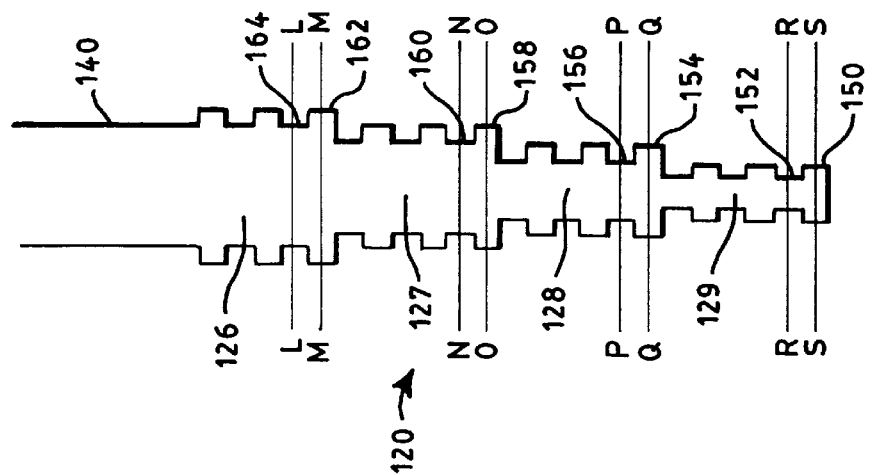
FIG. 6a is a cross section view of a post of this invention.

Referring to FIGS. 6a, 6b and 6c shows a post 140, root 122 with bore 138 and FIG. 6c shows post 140 of FIG. 6a in bore 138 of root 122 of FIG. 6b. Post 140 consists of a lower section 120 which is divided into subsections 126, 127, 128, and 129. These subsections have extensions 150, 154, 158 and 162 respectfully with subsections walls 152, 156, 158 and 164 respectfully. Extension 150 of subsection 129 of lower section 120 of post 140 has a diameter as is measured through line S—S and wall 152 of subsection 129 of lower section 120 of post 140 has a diameter as is measured through line R—R. Similarly, extension 154 is diameter Q—Q, subsection wall 156 is diameter P—P, extension 158 is diameter O—O, subsection wall 160 is diameter N—N, extension 162 is diameter M—M and subsection wall 164 is diameter L—L.

When post 140 is used in a slow speed drill it rotates at approximately 30,000 revolutions per minute. This speed means that all tooth structure is removed in a matching bore subsection with a resulting cylindrical shape. Lateral movement may make it out of round or create grooves in the bore wall which will further aid in cement retention and therefore post retention. The extension 150 forms bore subsection 136 of bore 138 of root 122 is diameter W—W such that diameter S—S of extension 150 is equal to it. A similar result occurs when subsections 128, 127, and 126 form subsections 134, 132, and 134 of bore 138 of root 122 respectfully such that diameter V—V equals Q—Q, U—U equals O—O and T—T equals M—M. FIG. 6b and 6c show the results of initial canal preparation.

A portion of the bottom portion 120 of post 140 is then removed by sectioning with customary dental burrs. Sectioning results in post 140 being a shorter length such that repositioning post 140 into bore 138 results in subsections 128, 127 and 126 of lower section 120 of post 140 engaging subsections 136, 134 and 132 of bore 138 of tooth root 122 respectfully. The diameter Q—Q, O—O AND M—M of extensions 154, 158, and 162 of subsections 128, 127 and 126 of lower section 120 of post 140 respectfully is larger than diameter W—W, V—V and U—U subsections 136, 134 and 132 of bore 138 of tooth root 122 respectfully such that extensions engage the walls of bore 138. Hand oscillation results in grooves cut in bore 138 walls as observed in FIG. 2. It is preferable to have the extensions of a lower segment smaller as measured from a radius of the center of post 140 than extensions of the subsection above it so as to maximize extension engagement of wall structure with the bore 138 of root 122. A maximum extension ratio would match the diameter of the subsection wall of the subsection above it. For example, diameter Q—Q of extension 154 of subsection 128 of lower portion 120 of post 140 would be the same diameter as N—N of subsection wall 160 of subsection 127, of lower section 120 of post 140. Diameter P—P of subsection wall 156 of subsection 128 of lower section 120 of post 140 would be the same diameter as S—S of extension 150 of subsection 129 of lower section 120 of post 140. The result is a subsection wall is the same diameter as the extensions on the subsection below it. Extension 150 of diameter S—S prepares a matching diameter W—W of subsection 136 of bore 138 of root 122. Because P—P of subsection wall 156 of subsection 128 of lower section 120 of post 140 is the same diameter as S—S and, therefore, W—W of subsection 136 of bore 138 of root 122, extension 154 will cut the wall of subsection 136 of bore 138 of root 122 but subsection wall 156 of subsection 128 of lower section 120 of post 140 will not effect cutting and will provide an exact fit to an existing dimension in bore 138 of root 122.

I claim:

1. A dental post shaped to fit into a canal of a tooth, which comprises:

an upper stem portion, a bottom portion attached to said upper stem portion, and positioned to extend into said canal, said bottom portion formed from a plurality of generally cylindrical sections each having a diameter different from remaining sections and having an extension adapted to extend toward a wall of said canal, a lowermost section of said plurality of sections having a smallest section diameter being the section most remote from said upper stem portion, an uppermost section of said sections having a largest section diameter being the section in closest proximity to said upper stem portion, said sections positioned between said lowermost section and said uppermost section having progressively larger diameters in a direction from said lowermost section to said uppermost section, said plurality of sections optionally including said lowermost section having means for cutting a wall of said canal when said post is rotate wthin said canal, said means comprising at least one groove in a wall portion of said plurality of sections, including said extensions which defines cutting edges, the remaining portion of said wall, excluding said at least one groove being a non-cutting surface.

2. The post of claim 1 wherein said bottom portion has more than one extension.

3. The posts of claim 1 or claim 2 wherein said lowermost section includes said at least one groove which defines cutting edges.

4. The post of claim 1 or claim 2 wherein said lowermost section is free of grooves.

5. The post of claim 1 or claim 2 wherein said lowermost section functions primarily as a guide.

6. The post of claim 1 or claim 2 wherein said uppermost section functions primarily as a guide.

7. The post of claim 1 or claim 2 wherein a section intermediate said lowermost section and said uppermost section functions primarily as a guide.

8. The post of claim 1 or claim 2 wherein a plurality of said sections are formed of at least two subsections, each having a diameter different from at least one other subsection.

9. The post of claim 1 or claim 2 wherein the sections and optionally the lowermost section includes two of said grooves.

10. The process of positioning a dental post within a tooth which comprises:

removing dentin from a canal of a tooth, positioning into said canal a post comprising:

an upper stem portion, a bottom portion attached to said upper stern portion, and positioned to extend into said canal, said bottom portion formed from a plurality of generally cylindrical sections each having a diameter different from remaining sections and having an extension adapted to extend toward a wall of said canal, a lowermost section of said plurality of sections having a smallest section diameter being the section most remote from said upper stem portion, an uppermost section of said sections having a largest section diameter being the section in closest proximity to said upper stem portion, said sections positioned between said lowermost section and said uppermost section having progressively larger diameters in a direction from said lowermost section to said uppermost section, said plurality of sections optionally including said lowermost section having means for cutting a wall of said canal when said post is rotated within said canal, said means comprising at least one groove in a wall portion of said plurality of sections, which defines cutting edges, said plurality of sections also including a wall portion free of said at least one groove and having a non-cutting surface, rotating or oscillating said post within said canal to form a shaped canal shaped into a form approximately the outer surface shape of said bottom portion, removing said post from said shaped canal, adding cement into said shaped canal and, reinserting said post into said shaped canal.

11. The process of claim 10 wherein said bottom portion of said post has more than one extension.

12. The process of claim 10 wherein said lowermost section of said post includes said at least one groove which defines cutting edges.

13. The process of claim 10 wherein said lowermost section of said post is free of grooves.

14. The process of claim 10 wherein said lowermost section of said post functions primarily as a guide.

15. The process of claim 10 wherein said uppermost section of said post functions primarily as a guide.

16. The process of claim 10 wherein a section of said post intermediate said lowermost section and said uppermost section functions primarily as a guide.

17. The process of claim 10 wherein a plurality of said sections of said post are formed of at least two subsections each having a diameter different from at least one other subsection.

18. The process of claim 10 wherein a plurality of said sections of said post and, optionally said lowermost section includes two of said grooves.

* * * * *